United States Patent [19]

Yamashita et al.

[11] Patent Number: 5,116,757
[45] Date of Patent: May 26, 1992

[54] MEVALONIC ACID-PRODUCING MICROORGANISM

[75] Inventors: Haruyuki Yamashita; Teiyu Shimada; Hiromu Sugiyama, all of Tokyo, Japan

[73] Assignee: Asahi Denka Kogyo Kabushiki Kaisha, Tokyo, Japan

[21] Appl. No.: 477,572

[22] Filed: Feb. 9, 1990

[30] Foreign Application Priority Data

Apr. 14, 1989 [JP] Japan .................................. 1-94927

[51] Int. Cl.⁵ ............................ C12N 1/16; C12P 7/40
[52] U.S. Cl. .................................... 435/255; 435/136; 435/911
[58] Field of Search ...................... 435/255, 136, 911

[56] References Cited

U.S. PATENT DOCUMENTS 3,617,447 11/1971 Arima et al. ...................... 435/136

FOREIGN PATENT DOCUMENTS 0281143 9/1988 European Pat. Off. .
0392346 10/1990 European Pat. Off. .

OTHER PUBLICATIONS

ATCC Catalogue of Fungi/Yeasts, 17th Edition, p. 148, 1987.
Keiji et al., Eur. J. Biochem., 164(3), 547-52, 1987.
Ikeura et al., Journal of Antibiotics, 41(8), pp. 1148-1150, 1988.
Hata et al., Plant Cell Physiol., 28(4), 709-14, 1987 (abstract).

Primary Examiner—Douglas W. Robinson
Assistant Examiner—Deborah K. Ware
Attorney, Agent, or Firm—Young & Thompson

[57] ABSTRACT

A mevalonic acid-producing microorganism which belongs to *Saccharomycopsis fibuligera* and is resistant to ML-236B.

3 Claims, No Drawings

MEVALONIC ACID-PRODUCING MICROORGANISM

BACKGROUND OF THE INVENTION

1. Field of the Invention

This invention relates to a mevalonic acid-producing microorganism. In particular, it relates to a melavonic acid-producing microorganism capable of producing mevalonic acid at a high yield.

It is know that mevalonic acid exists in the form of an acid and in the form of a lactone which may be readily converted into each other. Unless otherwise noted, the term "mevalonic acid" as used herein involves both of these forms.

2. Description of the Prior Art

Mevalonic acid, which was isolated by Wright et al. for the first time [cf. Journal of the American Chemical Society, 78, 5273-5275 (1956)], is known as an important intermediate in the synthesis of various isoprenoids such as cholesterol.

Further, mevalonic acid takes an important role in the metabolism in organisms. For example, it promotes the growth of various microorganisms, animals and/or plants. Therefore it is employed as a growth promoter for microorganisms, animals and plants. Furthermore, mevalonic acid is employed as a precursor for, e.g., pyrethroid agricultural chemicals, ubiquinone (respicoenzyme Q), dolichol (glycoprotein synthsizing factor) and fat-soluble vitamins.

Synthetic racemic mevalonic acid has been used for these studies, since natural (R-form) mevalonic acid is hardly available.

There is no method whereby natural mevalonic acid can be produced at a satisfactory yield by using a microorganism such as Saccharomycopsis fibuligera.

SUMMARY OF THE INVENTION

It is an object of the present invention to provide a mevalonic acid-producing microorganism capable of producing mevalonic acid at a high yield.

In order to achieve the above object, the present inventors have conducted extensive studies. As a result, they have found out that a strain belonging to Saccharomycopsis fibuligera and having a resistance to a specific compound has a highly selective productivity of mevalonic acid, thus completing the present invention.

Accordingly, the present invention provides a mevalonic acid-producing microorganism which belongs to Saccharomycopsis fibuligera and is resistant to ML-236B.

By using the mevalonic acid-producing microorganism of the present invention, therefore, mevalonic acid can be economically and readily obtained at a high yield.

DETAILED DESCRIPTION OF THE INVENTION

The mevalonic acid-producing microorganism of the present invention is a microorganism which belongs to Saccharomycopsis fibuligera, has an enzymatic system for the biosynthesis of mevalonic acid and is resistant to ML-236B.

As the mevalonic acid-producing microorganism of the present invention, any strain obtained either by newly isolating from nature or by mutagenesis, for example, a physical treatment such as irradiation with UV light, x-ray or γ-ray or a chemical treatment with the use of a chemical such as nitrosoguanidine may be used, so long as it satisfies the above-mentioned basic requirements.

Particular examples of strains satisfying these requirements include ADK 8107 (FERM BP-2320) and ADK 8108 (FERM BP-2321) each obtained by treating Saccharomycopsis fibuligera IFO 0107 with ML-236B. IFO means a stock strain conserved in the Institute for Fermentation, Osaka.

The compound ML-236B, which is the subject of the resistance test in the present invention, is compound of the following structure which is described in Japanese Patent Publication No. 12114/1981 and No. 5360/1984:

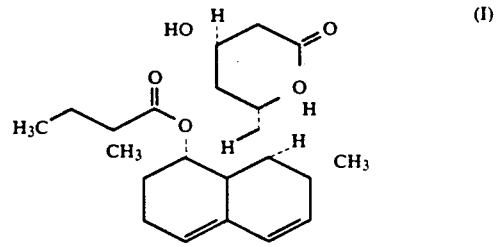

In the present invention, the expression "resistant to ML-236B" means that said strain can grow in a medium containing ML-236B. When a strain which has been incubated in a medium containing 0.0004% by weight, preferably 0.003% by weight and still preferably 0.02% by weight, of ML-236B at 25° C. for seven days under static conditions shows an absorbance $(A_1)$ at 660 nm that is 70% or above of absorbance $(A_0)$ at 660 nm incubated samely except no using ML-236B, namely, $(A_1/A_0) \times 100 \geq 70$, said the strain is deemed to be resistant to ML-236B.

The use of the mevalonic acid-producing microorganism of the present invention makes it possible to produce mevalonic acid at a high yield.

In order to produce mevalonic acid by using the mevalonic acid-producing microorganism of the present invention, a mevalonic acid-producing microorganism belonging to Saccharomycopsis fibuligera, preferably ADK 8107 (FERM BP-2320) and/or ADK 8108 (FERM BP-2321), each a variant of Saccharomycopsis fibuligera IFO 0107, is cultured and the mevalonic acid thus produced is recovered from the culture medium.

More particularly, the microorganism of the present invention may be cultured by a common method, for example, one described in U.S. Pat. No. 3,617,447 and the mevalonic acid thus produced may be recovered from the culture medium by a known method. It is preferable to effect the following process so as to produce mevalonic acid at a higher yield.

As the medium, one comprising 5 to 15% by weight of a carbon source, 0.5 to 3% by weight of an organic nitrogen source, 0.02 to 0.1% by weight of a nonionic surfactant capable of solubilizing the cell membrane of the microorganism, if required, and water (the balance) may be used. This medium may further contain, for example, phosphates, potassium salts, magnesium salts and calcium salts. Each of these additives may be preferably contained in an amount of from 0.01 to 5% by weight.

Furthermore, the medium may contain synthetic polymers and silicone antifoaming agents, without departing from the spirit of the present invention.

The mevalonic acid-producing microorganism of the present invention is inoculated into said medium and cultured therein at 20° to 40° C., preferably 25° to 35° C. When the culture is to be conducted under shaking, the shaking may be conducted at 150 to 200 rpm so as to elevate the efficiency. When it is to be conducted under aeration and agitation, the agitation may be conducted at 100 to 500 rpm and 0.2 to 1.5 vvm, preferably 200 to 400 rpm and 0.5 to 1.0 vvm, so as to elevate the efficiency.

It is further preferable to culture the microorganism for a given period of time under shaking and/or aerating and agitation, adding a substrate containing at least a carbon source to the culture medium one or more times and further continue the culture, thus efficiently producing mevalonic acid.

The mevalonic acid produced by using the microorganism of the present invention may be purified in a known manner. For example, the purification may be conducted as follows. After the completion of the culture, the cells are removed from the culture medium by a known method such as centrifugation or filtration through an organic synthetic membrane. Next, the culture medium is purified by a conventional method, for example, purification with the use of a reverse osmosis membrane, silica gel, an ion exchange resin or a porous polymer resin, solvent extraction with the use of ethyl acetate or methyl ethyl ketone, distillation under reduced pressure, molecular distillation or crystallization.

To further illustrate the present invention, and not by way of limitation, the following Examples and Comparative Example will be given.

In the following Examples and Comparative Example, mevalonic acid was determined by the following method.

Determination of mevalonic acid 1.0 ml of a sample was collected in a test tube and acidified by adding five or six drops of 50% (W/W) phosphoric acid. Next, 1 g of anhydrous $Na_2SO_4$ was added thereto. 2.0 ml of ethyl acetate was further added thereto and the obtained mixture was stirred for 30 seconds. The mixture was centrifuged in a rotator of 14 cm in radius at 2500 rpm. The upper ethyl acetate phase was introduced into another test tube A and evaporated to dryness. To the lower aqueous phase was added 2.0 ml of ethyl acetate followed by stirring for 30 seconds. The mixture was similarly centrifuged. The upper ethyl acetate phase was introduced into the test tube A and evaporated to dryness. The same procedure was repeated to thereby give 6 ml, in total, of the dried ethyl acetate phase. This dry product was dissolved in 1 ml of isopropanol containing 10 mg/ml of δ-valerolactone (a product of Aldrich Chemical Co.) as an internal standard, and subjected to high-performance liquid chromatography (HPLC) under the following conditions:

column: Nucleosil 5N $(CH_3)_2$ (a product of M. Nagel, West Germany), 4.6 $\phi \times 250$ mm, 40° C.

mobile phase: N-hexane/isopropanol (9/1), 2.0 ml/min.

detector: differential refractometer (SE-61, mfd. by Showa Denko K.K.)

injection: 5 ul.

Evaluation of resistance 5 ml of a medium comprising 0.67% by weight of a medium for testing the metabolism of carbon compounds (Bacto-yeast nitrogen base, a product of the Difco Inc. Laboratories), 0.5% by weight of glucose and the balance of water and an aqueous solution of ML-236B were separately sterilized. Prior to the inoculation, there materials were mixed aseptically together so as to give a predetermined ML-236B concentration. 0.2 ml of a suspension containing one platinum loopful of cells in 3 ml of sterilized physiological saline solution was inoculated into this medium and incubated therein at 25° C. under static conditions. For control, the same strain was inoculated into a medium free from ML-236B and incubated therein.

The resistance was evaluated by monitoring the growth of the strain by using the absorbance at 660 nm as an indication while comparing with the control case. When the absorbance ($A_1$) of the test case where ML-236B was used amounted to 70% or more based on that of the control one ($A_0$) on the seventh day, the strain was deemed to be resistant to ML-236B.

EXAMPLES 1 AND 2 COMPARATIVE EXAMPLE 1

20 l and 200 ml of a medium comprising 10% by weight of glucose, 0.05% by weight of polypeptone (a product of Nippon Seiyaku K.K.), 1.0% by weight of corn steep liquor (a product of Nippon Shokuhin Kako K.K.), 0.1% by weight of $KH_2PO_4$, 0.05% by weight of $MgSO_4 \cdot 7H_2O$, 1% by weight of $CaCO_3$, 0.05% by weight of a polyether antifoamiong agent (Adekanol; a product of Asahi Denka Kogyo K.K.) and the balance of water was prepared. One platinum loopful of *Saccharomycopsis fibuligera* ADK 8107 (FERM BP-2320) was inoculated into 200 ml of this medium and cultured therein at 28° C. under shaking for three days. Then the obtained culture medium was inoculated into 20 l of said medium and cultured therein at 28° C. and at 300 rpm under aerating at 20 l /min while monitoring the glucose concentration, pH and dissolved oxygen concentration. On the third day and seventh day of the culture, 2.0-kg portions of a 50% by weight aqueous solution of glucose were added to the culture. After effecting the culture for 12 days in total, the culture was ceased. After the completion of the culture, the mevalonic acid in the culture medium determined by the above-mentioned process was 19000 μg/ml (Example 1).

The procedure of Example 1 was repeated except that the *Saccharomycopsis fibuligera* 8107 (FERM BP-2320) was replaced by ADK 8108 (FERM BP-2321). Thus 19400 μg/ml of mevalonic acid was obtained (Example 2).

The procedure of Example 1 was repeated except that the *Saccharomycopsis fibuligera* 8107 (FERM BP-2320) was replaced by IFO 1745. Thus 10600 μg/ml of mevalonic acid was obtained (Comparative Example 1).

The resistance of each strain to ML-236B was examined. Table 1 shows the mevalonic acid productivity and the ratio of the absorbance to that of the control {($A_1/A_0) \times 100$} depending on ML-236B concentration of each strain.

TABLE 1

| Strain | | $(A_1/A_0) \times 100$ (%) ML-236B concentration (% by wt.) | | | Mevalonic acid productivity (μg/ml) |
|---|---|---|---|---|---|
| | | $0.4 \times 10^3$ | $3.0 \times 10^3$ | $20 \times 10^3$ | |
| Ex. 1 | ADK8107 | 98 | 95 | 86 | 19000 |
| Ex. 2 | ADK8108 | 97 | 96 | 84 | 19400 |
| Comp. Ex. 1 | IFO1745 | 65 | 15 | 1 | 10600 |

What is claimed is:

1. A biologically pure culture of a mevalonic acid-producing microorganism selected from the group consisting of *Saccharomycopsis fibuligera* FERM BP-2320 and *Saccharomycopsis fibuligera* FERM BP-2321, said microogranism being resistant to ML-236B such that said microorganism, after seven days incubation in a medium containing 0.02% by weight ML-236B at 25° C., has an absorbance $A_1$ at 660 nm that is at least 70% of an absorbance $A_0$ at 660 nm of said microorganism incubated under otherwise identical conditions in a medium free of ML-236B.

2. The culture according to claim 1, wherein said microorganism is *Saccharomycopsis fibuligera* FERM BP-2320.

3. The culture according to claim 1 wherein said microorganism is *Saccharomycopsis fibuligera* FERM BP-2321.

* * * * *